US007234653B2

(12) United States Patent
Powell et al.

(10) Patent No.: US 7,234,653 B2
(45) Date of Patent: Jun. 26, 2007

(54) PORTABLE SELF-CONTAINED MISTING SYSTEM

(76) Inventors: Bruce B. Powell, 13333 High Country La., #10, Herriman, UT (US) 84065; Mark W. Platt, 12247 S. 1860 West, Riverton, UT (US) 84065

( * ) Notice: Subject to any disclaimer, the term of this patent is extended or adjusted under 35 U.S.C. 154(b) by 156 days.

(21) Appl. No.: 10/938,477

(22) Filed: Sep. 10, 2004

(65) Prior Publication Data

US 2005/0077391 A1 Apr. 14, 2005

Related U.S. Application Data

(60) Provisional application No. 60/502,733, filed on Sep. 12, 2003.

(51) Int. Cl.
*A61M 11/02* (2006.01)
*B05B 9/04* (2006.01)
*A01G 27/00* (2006.01)

(52) U.S. Cl. ........................ 239/373; 239/302; 239/70; 239/566; 239/337; 239/332; 239/266; 222/333; 137/312

(58) Field of Classification Search ................ 239/120, 239/268, 70, 67, 289, 211, 273, 276, 330, 239/351, 152–159, 566, 532, 337, 373, 74, 239/128, 146, 132, 22, 23, 332, 266, 269, 239/271, 272
See application file for complete search history.

(56) References Cited

U.S. PATENT DOCUMENTS 1,140,453 A * 5/1915 Frank ......................... 222/385
3,901,449 A * 8/1975 Bochmann .................. 239/332
5,330,104 A * 7/1994 Marcus ....................... 239/266
5,338,165 A * 8/1994 Brockner et al. ........ 417/423.1
5,390,852 A * 2/1995 Schuenemann et al. .. 239/263.1
6,112,538 A 9/2000 Strussion
6,158,669 A * 12/2000 Louis ......................... 239/146
6,182,463 B1 2/2001 Strussion et al.
6,189,805 B1 2/2001 West et al.
6,367,278 B1 4/2002 Strussion et al.
6,386,835 B1 5/2002 Kalpakoff
6,592,049 B1 * 7/2003 Wolput ........................ 239/70
6,817,206 B2 * 11/2004 Shahbaz ...................... 62/331
6,886,759 B1 * 5/2005 Okronick et al. ........... 239/289
7,007,826 B2 * 3/2006 Shapanus et al. ........... 222/175

* cited by examiner

*Primary Examiner*—Kevin Shaver
*Assistant Examiner*—James S. Hogan

(57) ABSTRACT

A portable misting system having a pump that is at least partially submersed in a fluid. The partial submersion of the pump enables the pump to move fluid through a supply hose to a plurality of misting nozzles. In one embodiment, the misting system includes a receptacle configured to receive and store a fluid. The pump is coupled to the receptacle so as to be at least partially submersed in the fluid contained therein. In another embodiment, the misting system includes a receptacle in fluid communication with a pump chamber. The pump is partially disposed within the pump chamber so as to be at least partially submersed in the fluid contained in the pump chamber.

41 Claims, 9 Drawing Sheets

PORTABLE SELF-CONTAINED MISTING SYSTEM

CROSS-REFERENCE TO RELATED APPLICATIONS

This application claims the benefit of U.S. Provisional Patent Application Ser. No. 60/502,733, filed Sep. 12, 2003, and entitled "Portable Self-Contained Misting System"," which is incorporated herein by reference.

BACKGROUND OF THE INVENTION

1. The Field of the Invention

The present invention generally relates to misting systems. More particularly, the present invention relates to a self-contained portable misting system with an integrated pump, power supply, and storage chamber.

2. The Related Technology

During summer months, outdoor events such as sporting events, trade shows, and social gatherings are often carried out in uncomfortable or even extreme heat. Since weather cannot be controlled, a planned event often takes place despite hot weather.

In some cases, heat plays a role in injury. For instance, athletes or fans at a sporting event may suffer from heat exhaustion. In other instances, hot weather is not life threatening or injurious, but the heat makes attendees uncomfortable. Many people in today's society have grown accustomed to modern conveniences such as air conditioning and greatly enjoy conditioned surroundings.

Unfortunately, outdoor events cannot be air-conditioned. However, systems have been developed to cool people at outdoor events. One such system uses water and a misting system that sprays water out of nozzles with fine pores. The fine pores cause the water to spray out as a mist suspended in air.

Mists of water have the potential of cooling down surrounding air. Energy is required to change water from a liquid state to a gaseous state. A mist water is able to cool down its surroundings because it draws energy out of the surrounding air to change the water from the liquid state to the gaseous state. Water is a particularly useful liquid to use in a misting system because it is cheap and has a high heat capacity.

Several systems for cooling outdoor events are known, such as built in misting systems at sporting events. Home misting systems also exist. However, typical misting systems are too awkward for convenient, portable use, particularly for large groups of people.

Therefore, what is needed is a portable misting system that provides outdoor cooling by spraying mists of water, but does not require cumbersome extension cords or hoses.

BRIEF SUMMARY OF THE INVENTION

Embodiments of the present invention provide a self-contained portable misting system that overcomes the problems with the portable misting systems discussed above. In an exemplary embodiment of the invention, a self-contained portable misting system is provided that does not require an extension cord or a connected water supply to operate. In one version of the misting system of the present invention, the self-contained portable misting system has a housing. The housing includes a receptacle, a dry compartment, and a pump chamber. The receptacle and pump chamber are in fluid communication with one another.

A pump, such as a submersible pump, has a lower end that is disposed within the pump chamber. The pump has electrical wires extending from an upper end thereof, which is disposed in the dry compartment. The electrical wires extend from the upper end of the pump to a power supply, such as a battery, disposed within the dry compartment. A fluid supply hose also extends from the pump and has at least one misting nozzle attached thereto. Thus, the supply hose is in fluid communication with the pump and the misting nozzle. In another embodiment, the pump is not a submersible pump. Instead, the pump is housed in the dry compartment and is coupled to a hose that extends into the pump chamber.

In one embodiment, the dry compartment is L-shaped, such that a first portion of the dry compartment extends over the pump chamber, while the remaining portion of the dry compartment (e.g., the portion that receives the battery) is adjacent the pump chamber.

In one exemplary embodiment, the portable, self-contained misting system of the present invention allows a person to mist a location that does not have access to a water source or electrical outlets. Prior to attending an outdoor event, a person using the system of the present invention simply fills the receptacle with water and charges the power supply. The hoses, nozzles, power and water all fit within the housing and are easily transported to the outdoor event. In addition, the housing has a system connected thereto for selectively moving the water misting system, such as a wheel assembly with a retractable handle.

The misting system creates a mist when the pump is turned on and the pump pumps water into the supply hose to create pressure therein. The fluid pressure in the supply hose causes the misting nozzles to spray a mist of fluid.

The compact portable system allows those attending a sporting event, trade show or social gathering to provide their own misting. In the exemplary embodiment, because the system is self contained, there is no need to find power or water sources at the site of the outdoor event.

The portable misting system is useful for a variety of different outdoor purposes, particularly when the weather becomes extremely hot. For example, the mister can be used at picnics, athletic events, trade shows, and a variety of different games and activities in which it is desirable to cool ones body temperature. For example, in one embodiment the mister is used in the dugout wherein the misting heads are placed on the fence or wall of the dugout in order to cool a baseball or softball team. In another embodiment, the misting heads are connected to an awning, a wall, or a fence, or other assembly enabling it to be used at a party or sales event, family picnic, or other outdoor activity.

BRIEF DESCRIPTION OF THE DRAWINGS

To further clarify the above and other advantages of features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
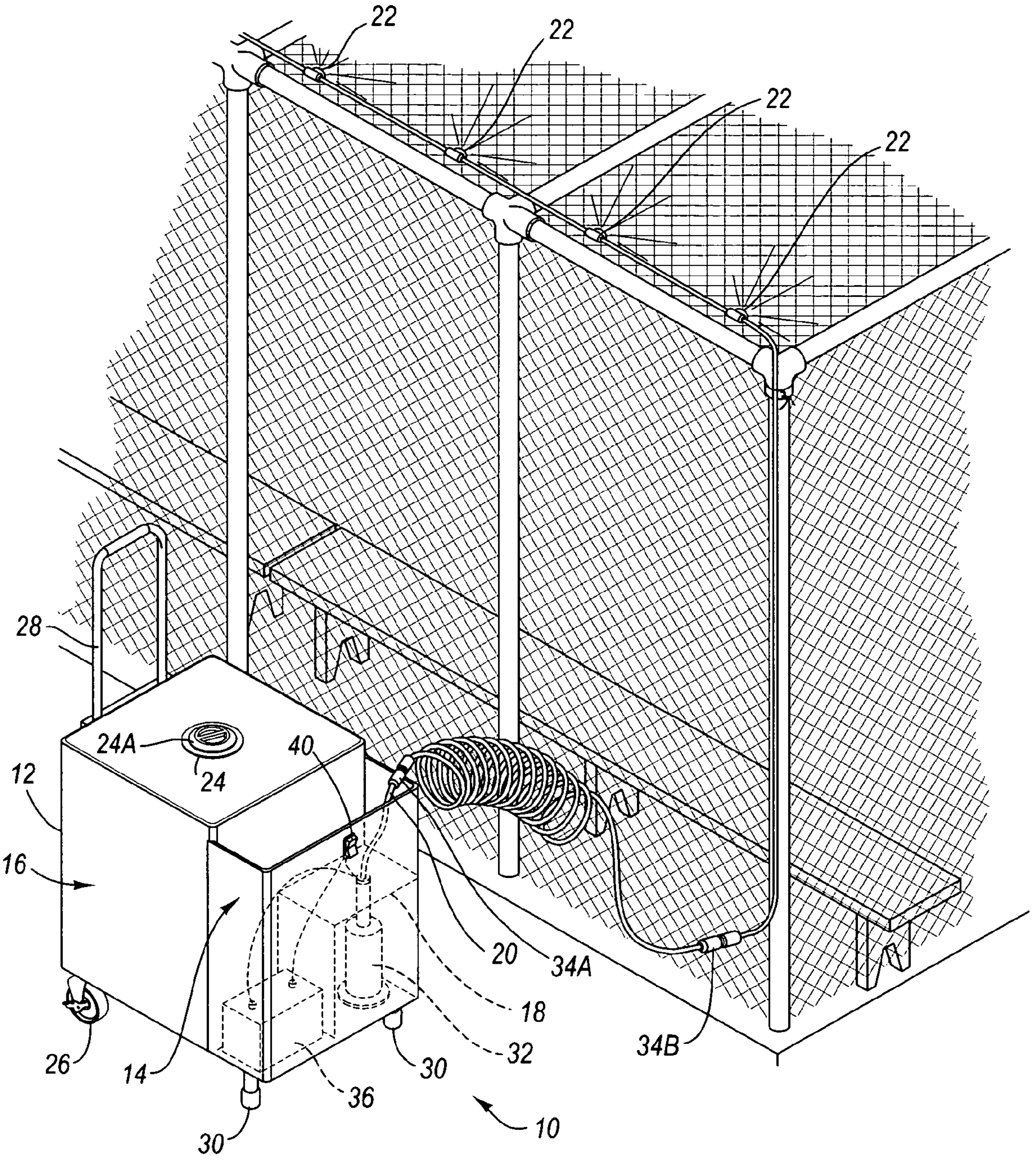
FIG. 1 shows a perspective view of an exemplary embodiment of a portable, self-contained misting system of the present invention.

FIG. 1 shows an exemplary embodiment of a misting system 10 according to the present invention. Misting system 10 has a housing 12. Housing 12 has an L-shaped dry compartment 14 and a receptacle 16. Receptacle 16 is configured to store a liquid such as water. A pump chamber 18 is formed at a bottom corner of housing 12. Pump chamber 18 is in fluid communication with receptacle 16.

A supply hose 20 has a plurality of misting nozzles 22. Supply hose 20 receives water from a pump 32 and delivers it to misting nozzles 22. Misting nozzles 22 are configured to spray the water from pump 32 to create a mist that will cool the surrounding air.

In one embodiment housing 12 is made of plastic and receptacle 16 and pump chamber 18 are configured to hold between about five and about seven gallons of water. The size of housing 12 greatly depends on the size of receptacle 16, which significantly depends on the desired amount of liquid (e.g., water) to be misted. Nevertheless, receptacle 16 can be any desired size. For instance, a five to seven gallon receptacle may be sufficient for an individual or family. On the other hand a larger receptacle may be useful for larger groups of people or for commercial use.

Pump chamber 18 is placed at a bottom corner of housing 12. When mister system 12 is stationary and level, the bottom of chamber 18 is as low or lower than receptacle 16. Such a configuration allows all the water in receptacle 16 to flow into pump chamber 18 under gravitational forces.

Housing 12 also defines a top inlet 24 to receptacle 16. A top lid 24A covers top inlet 24. Receptacle 16 is filled with water, or other liquid to be misted, through inlet 24. A pair of wheels 26 and a retractable handle 28 are also connected to housing 12 to provide mobility to misting system 10. In an exemplary embodiment, handle 28 and wheels 26 are connected to housing 12 opposite dry compartment 14.

Misting system 10 can be rotated onto its wheels and maneuvered using retractable handle 28. A stop 30 (e.g., an adjustable stop) is placed opposite wheels 26. Stop 30 prevents misting system 10 from moving when misting system 10 is in a desired stationary position. Stop 30 can also be adjusted to maintain misting system 10 level when misting system 10 is placed on uneven surfaces.

Figure 2:
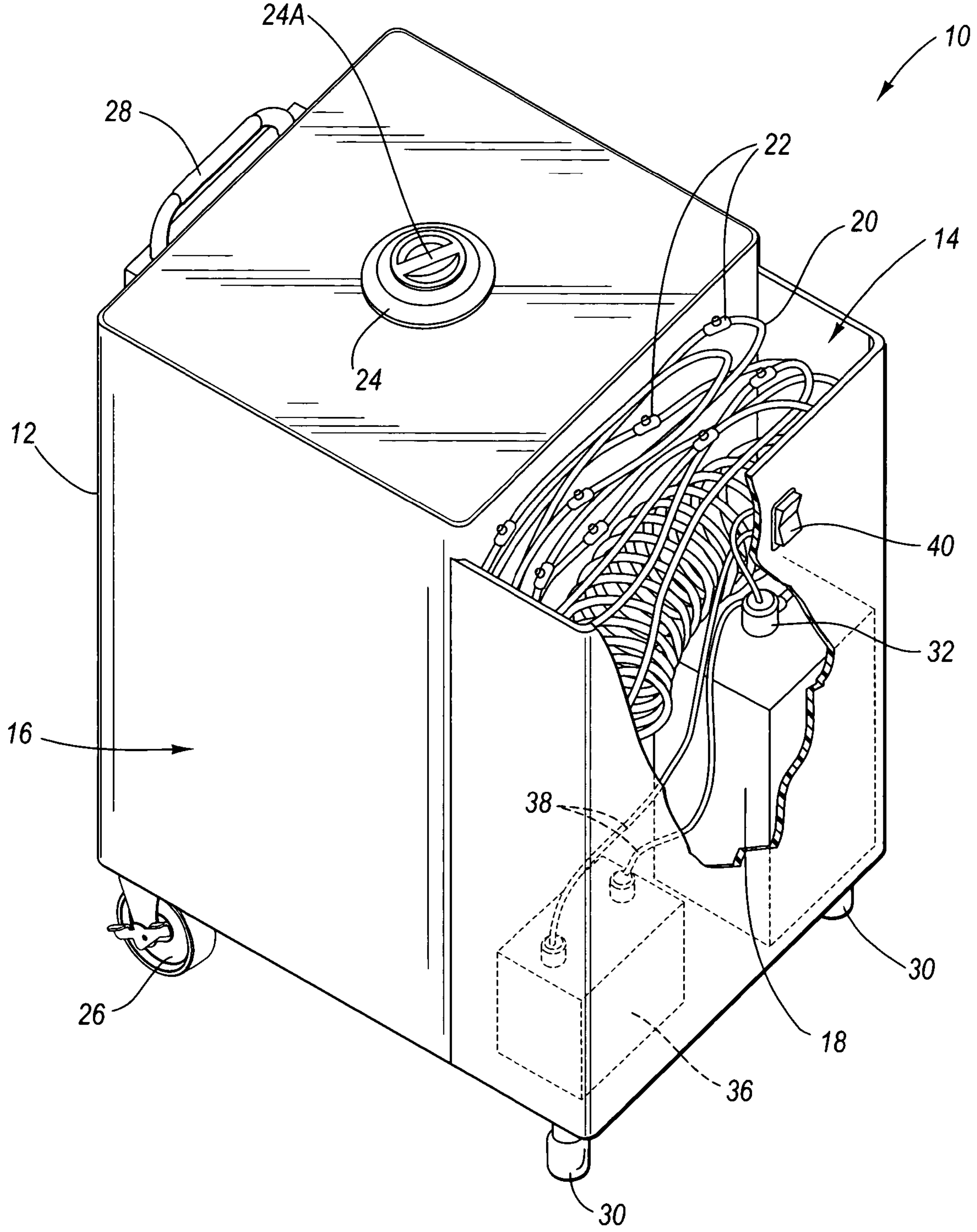
FIG. 2 shows a top perspective view of the misting system of FIG. 1.

As shown in FIG. 2, the lower end of pump 32 is disposed in pump chamber 18. A power supply 36, such as a rechargeable battery, is disposed in the bottom of L-shaped dry compartment 14 adjacent pump chamber 18. Pump 32 is electronically connected to power supply 36 through electrical wire 38.

Pump 32 may be a 12-volt pump. In one embodiment, pump 32 can be a fuel pump of the type used in automobile gas tanks. In the case of a submersible pump, pump 32 is partially submersed in water and the water acts as a cooling system such that no separate cooling system is needed for pump 32. In one embodiment, pump 32 is configured to provide between about sixty to about ninety pounds per square inch (60–90 psi) of pressure. In the case where a 12-volt battery is the means for providing power, in one embodiment the pump would draw only seven (7) amps per hour.

Power supply 36 is selected for operation with pump 32. In one embodiment, power supply 36 is a rechargeable 12 volt battery. Any type of 12 volt battery can be used with the present invention so long as the battery has proper voltage and power to run pump for the period of time needed to pump most or all of the water out of receptacle 16.

Figure 1A:
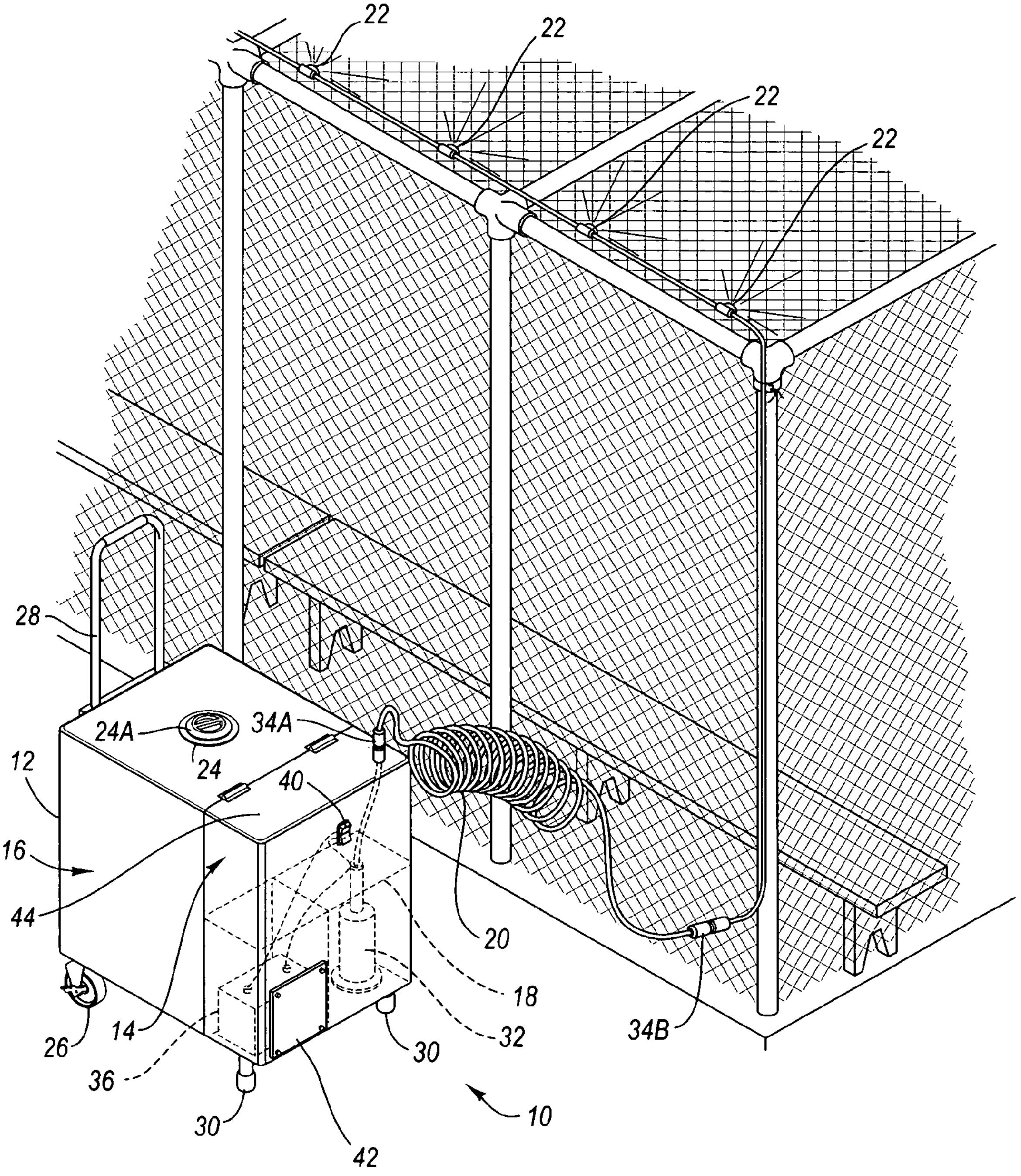
FIG. 1A shows a perspective view of an alternate design of the self-contained misting system of the present invention having a front access door for the battery and a hinged door covering to selectively cover the dry compartment.
Figure 3:
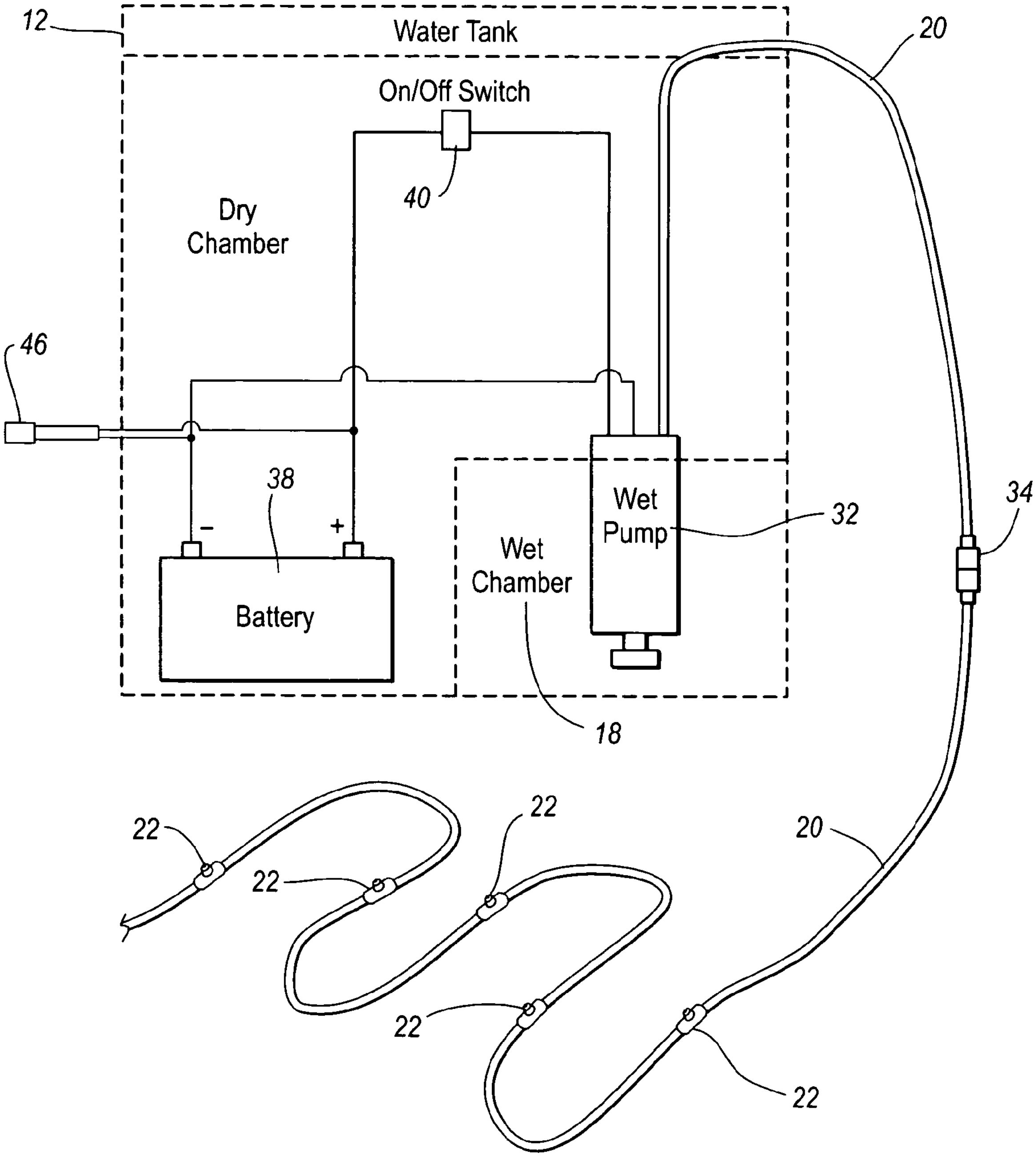
FIG. 3 shows a schematic of the misting system of FIG. 1.

In another embodiment, the power supply 36 also has a plug 46 (e.g., a 110 volt plug), as depicted in FIG. 3, that may be used to connect power supply 36 to a power source to charge power supply 36 or to provide a secondary power source. In another embodiment, power supply 36 plugs into a cigarette lighter of a vehicle. In one embodiment, a door 42 (FIG. 1A) is connected to housing 12 such that power supply 36 can be removed from a side of housing 12 rather than from the top. A top door 44 (FIG. 1A) or other panel can also be placed over the power source and pump and/or the entire dry compartment. Such door or panel over the pump may have an opening through which the supply hose 20 extends.

FIG. 3 shows a schematic of dry compartment 14 and pump chamber 18. Power supply 36 is electronically connected to pump 32 through electrical wire 38. In one embodiment, misting system 10 has an on/off switch positioned on wire 38 between power supply 36 and pump 32. A user turns pump 32 on and off at the switch 40.

In another embodiment, an input device and display panel electronically connect to wire 38. The display panel may indicate the battery life remaining and may provide a meter or gauge of power usage and/or time remaining. The meter or gauge may include LEDs. The input device may also have an automatic shut off device configured therein to shut pump 32 off when pump chamber 18 no longer has water therein. Those of ordinary skill in the art would understand and appreciate the vast number of configurations and component arrangements of an automatic shut off device, including differing types and placements of required sensors and electrical devices associated with an automatic shut off device.

In an exemplary embodiment, pump 32 has one or more filters at a bottom end where pump 32 intakes water from pump chamber 18. A sock filter may be positioned outside of pump 32 over a second filter, which may be positioned on an intake chamber on the bottom of pump 32. The double filter system ensures that particles large enough to plug a misting nozzle do not flow through the misting system 10. Pump 32 may be removable so that the filters can be regularly cleaned.

As shown in FIG. 3, supply hose 20 is connected to pump 32. Pump 32 is in fluid communication with supply hose 20 and provides a desired pressure in supply hose 20. Pump 32 may have a pressure release valve that lets water pass back into pump chamber 18 to ensure that pressure in supply hose 20 does not increase above a desired pressure. A quick connector 34A may couple supply hose 20 to pump 32. An alternative or additional quick connector 34B may be position after the coiled portion of supply hose 20.

Supply hose 20 has a plurality of misting nozzles 22, coupled thereto. Supply hose 20 also has clips, for example, alligator clips, such that supply hose 20 may be attached to various items such as a covering, dugout, chair, tent, or even the retractable handle 28 in housing 12. The housing 12 may also have posts to wrap supply hose around. For example, in one embodiment, supply hose 20 is wrapped around external posts coupled to the housing, similar to the wrapping of a vacuum electrical cord for storage on the vacuum. In another embodiment, supply hose 20 is short such that it only reaches the length needed to clip a nozzle to the handle 26, when handle 28 is in the contracted or the extended position.

Mister nozzles 22 may have any desired flow rate. The flow rate of nozzles 22 is optimized to provide adequate misting but minimize water and power usage. In addition, supply hose 20 may be any length and may have any number of nozzles. Supply hose 20 may also have a portion that is coiled to facilitate storing supply hose 20 in dry compartment 14.

In one embodiment, an electrical plug or cord 46 may be utilized to allow a user to power the misting system by an external source. For instance, in one embodiment, cord 46 is configured to plug into an electrical socket or outlet. This enables the pump 32 of the misting system 10 to be actuated using a power source 36 other than one contained within the dry compartment 14. In another embodiment, cord 46 is configured to fit within the female receptacle of an automobile cigarette lighter.

Figure 4:
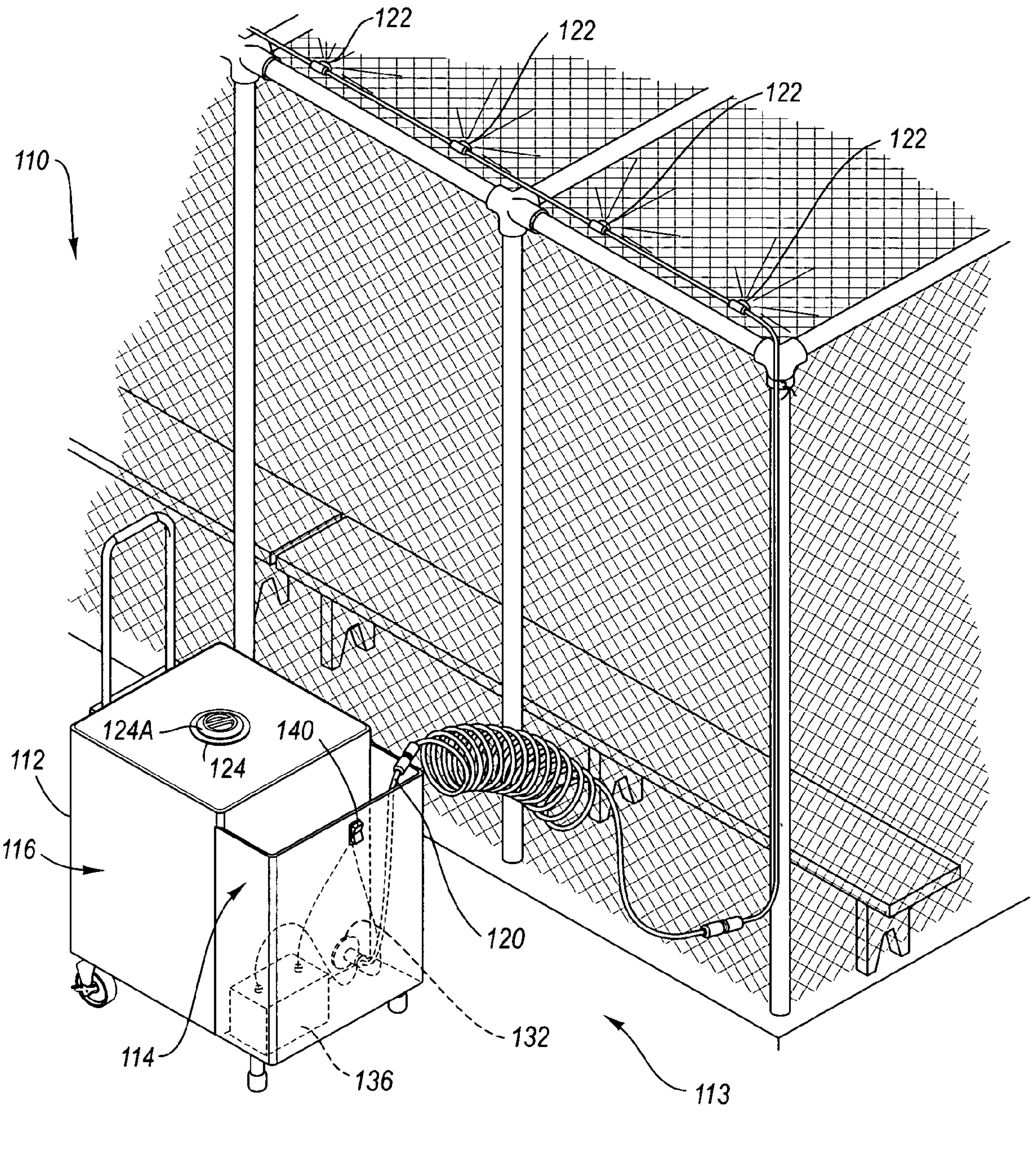
FIG. 4 shows a perspective view of an alternative embodiment of a portable, self-contained misting system of the present invention.

FIG. 4 shows an alternative embodiment of the misting system 110 according to the present invention, wherein the housing 112 does not feature a pump chamber 18 that is separate from receptacle 16, 116. In this embodiment, misting system 110 has a housing 112 and a misting assembly 113. Housing 112 includes a dry compartment 114 coupled to a receptacle 116. Dry compartment 114 is coupled to receptacle 116 to facilitate self-containment of misting system 110.

Misting assembly 113 includes (i) a pump 132, (ii) a power supply 136 for providing power to the pump 132, (iii) a supply hose 120, and (iv) a plurality of misting nozzles 122. Pump 132 is directly coupled to a wall of the receptacle 116 rather than being contained in a pump chamber 18 as shown in FIGS. 1–2. A more simplified design is achieved by coupling pump 132 directly to receptacle 116.

In the exemplary embodiment, pump 132 is mounted to a side wall of receptacle 116 in a horizontal fashion with at least a portion of the pump 132 disposed within receptacle 116. Mounting pump 132 in such a fashion and orientation enables pump 132 to be in fluid communication with the receptacle 116. The pump 132 being in fluid communication with the receptacle 116 enables the pump 132 to displace fluid from the receptacle 116 to the supply hose 120 when the pump 132 is activated.

Figure 4A:
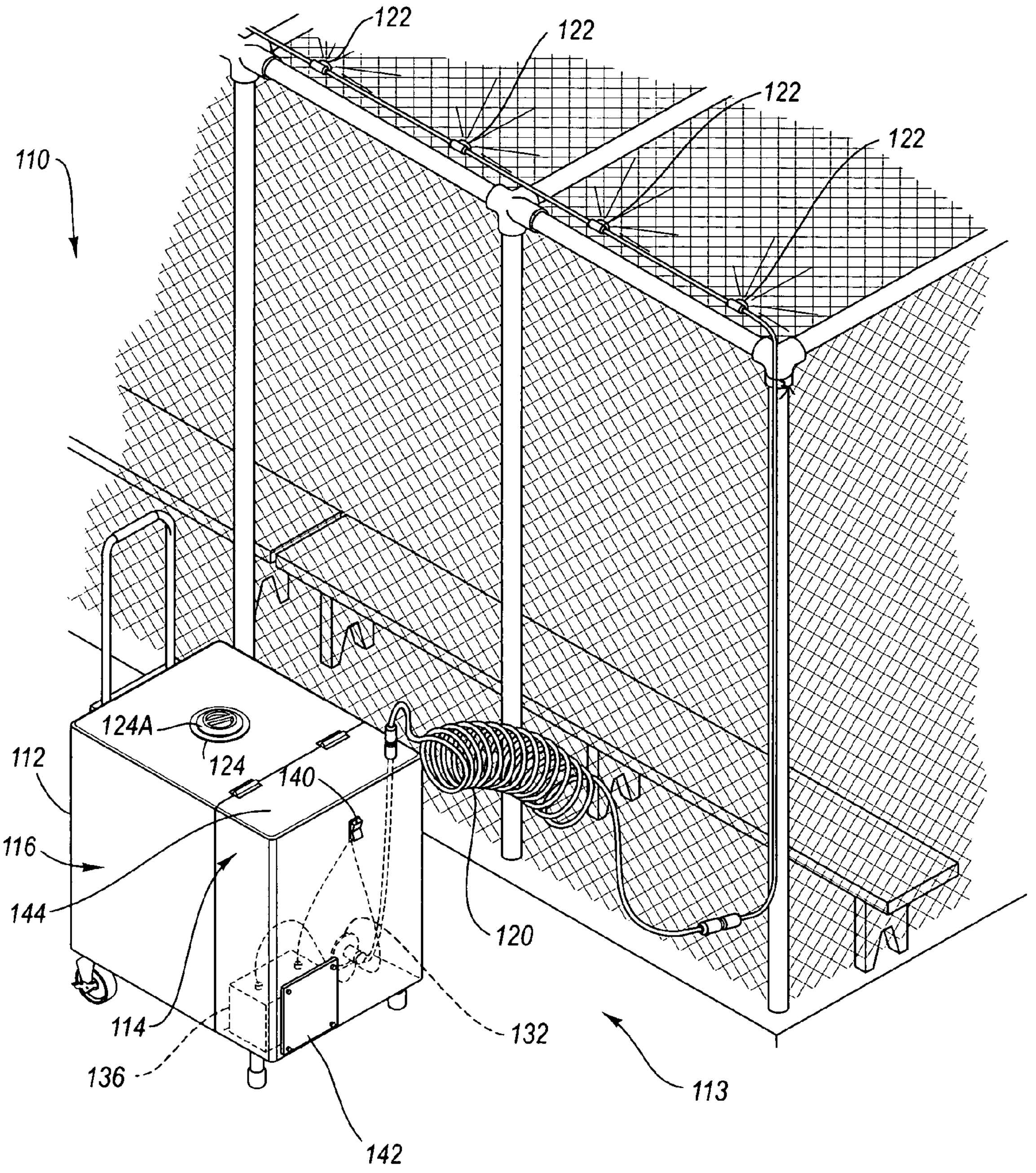
FIG. 4A shows a perspective view of an alternative design of the embodiment depicted in FIG. 4.

In one embodiment, the power supply 136 for providing power to the pump 132 is a battery, which is an example of a means for providing power to the pump 132. Another example of a means for providing power to the pump 132 is an electrical cord 46 that is configured to fit within an electrical outlet, or a plug 46 to be used with an automobile cigarette lighter, or the like. In this embodiment, the battery is housed in dry compartment 114 for use in activating pump 132. Supply hose 120 is connected to pump 132 at one end and to a plurality of misting nozzles 122 at an opposing end. Supply hose 120 facilitates transport of liquid from pump 132 to misting nozzles 122. Dry compartment 114 is configured to receive and house supply hose 120 and misting nozzles 122 when not in use. In an alternative design, as depicted in FIG. 4A, dry compartment 114 includes top door 144 and side door 142, each facilitating access to dry compartment.

Figure 5:
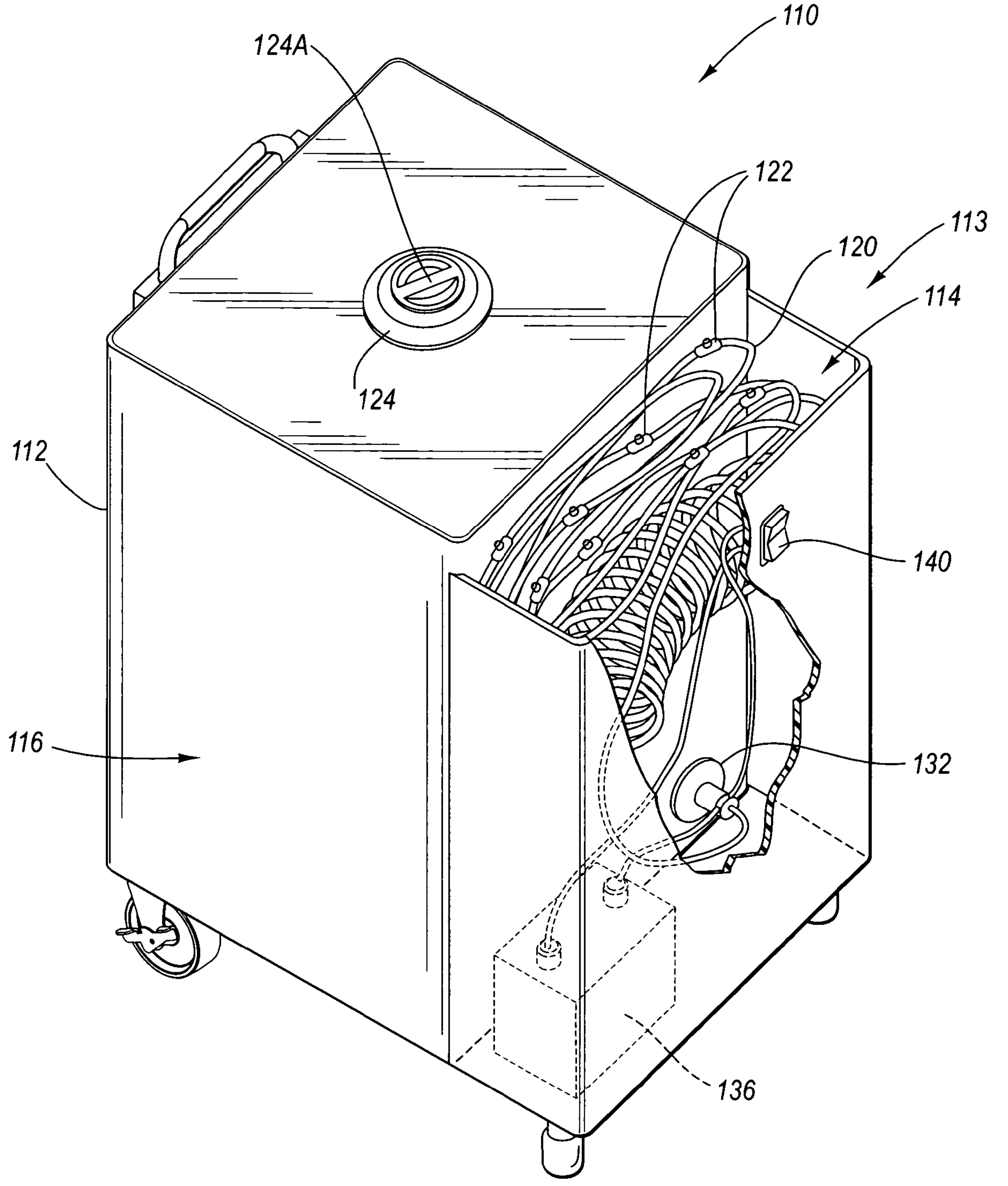
FIG. 5 shows a top perspective view of the misting system of FIG. 4.

As shown in FIG. 5, the pump 132 is secured on the lower portion of a side of receptacle 116 with at least a portion of pump 132 being disposed within receptacle 116. At least a portion of the pump 132 is disposed within receptacle 116 to facilitate displacement of fluid from receptacle 116 to misting nozzles 122 and to simultaneously cool the pump 132. In this respect, a main body portion 160 (see FIG. 5A) of the pump 132 is in direct contact with the liquid in the receptacle 116, or in other words, is partially submersed in the liquid. This placement of the pump 132 enables the pump 132 to be in fluid communication with the liquid contained in the receptacle 116. In addition, a pump that is partially submersed in a fluid provides many other benefits. For example, a submersible pump is cooled internally by the liquid being pumped. A pump that is cooled by the liquid it pumps reduces inefficiency and costly hardware associated with cooling the pump. Reducing the amount of hardware benefits the user monetarily and by reducing the weight and size of the system. In addition, a submersible pump operates at a lower decibel level and is quieter than operationally equivalent non-submersible pumps. Hence, use of the disclosed misting system 110 provides for a quieter, lighter, less expensive and less bulky portable misting system 110.

In one embodiment, a submersible pump 132 comprises a fuel pump of the type used in automobile gas tanks. In another embodiment, a submersible pump 132 comprises a fuel pump having certain modifications done thereto to enable a fluid, such as water, to pass therethrough without corroding the internal parts of the pump. The modifications may include providing a coating of corrosion-resistant material around any part that is corrosion susceptible. Another modification may include replacing the corrosive susceptible parts with different non-corrosive materials. In one embodiment, pump 132 is configured to provide between about sixty to about ninety pounds per square inch (60–90 psi) of pressure. In one embodiment wherein the power supply 138 is a 12-volt battery, the pump 132 is efficient enough to draw a mere seven (7) amps per hour. An example of a fuel pump can be found on page 7 of the Delphi "2003 Fuel Pump Catalog" under the title *Medium- and High-Pressure Twin Turbine Fuel Pumps*. The 2003 Fuel Pump Catalog can be located on the internet by selecting the file "Fuel Pump Catalog—Complete.pdf" at the following link:

http://go.delphi.com/del/DPSS_papercatalog/.

Figure 5A:
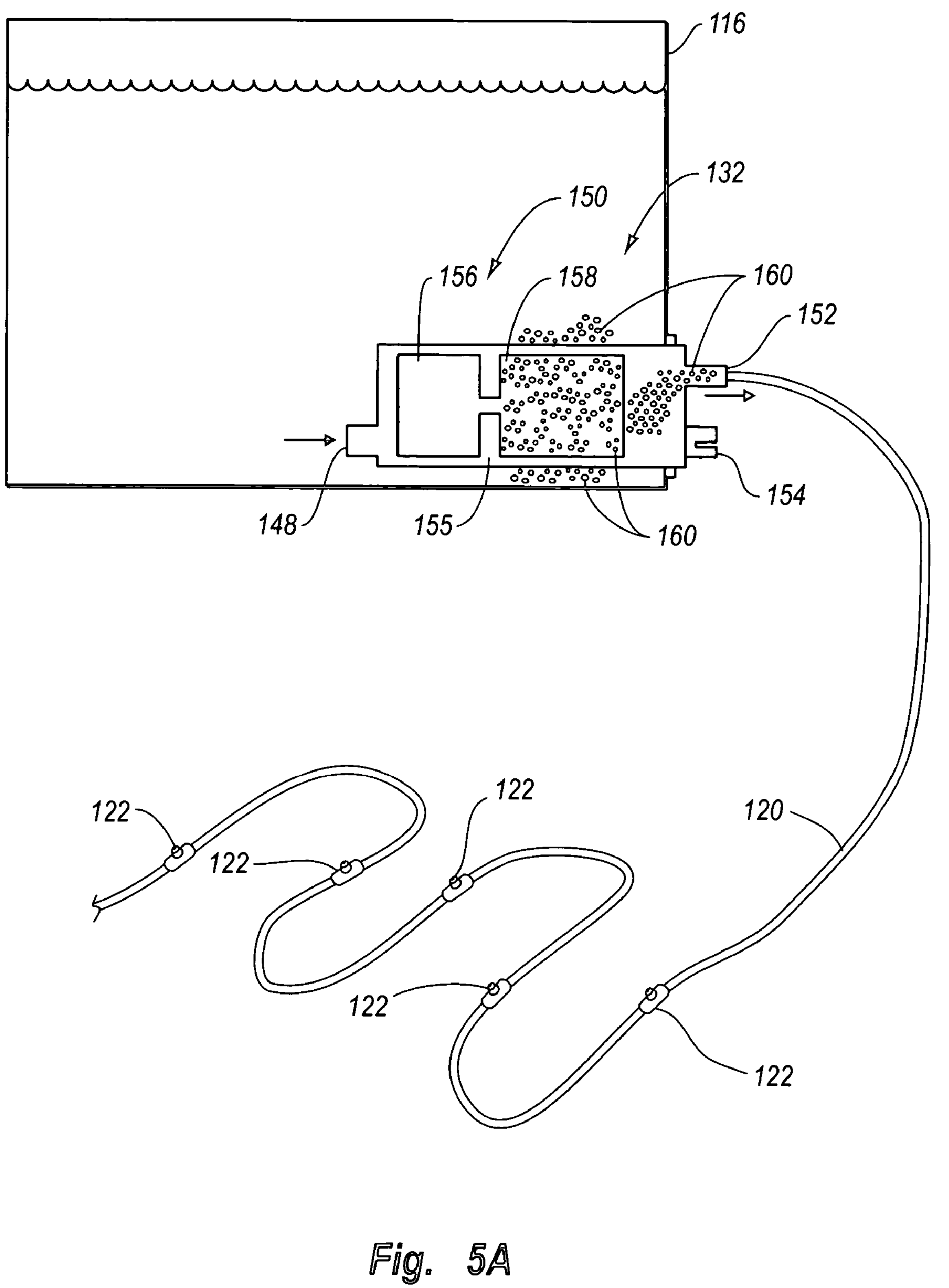

FIG. 5*a* is a schematic view of one example of the pump 132 of FIGS. 4 and 5. In one embodiment, pump 132 comprises (i) an inlet 148, (ii) a main body portion 150, (iii) an outlet 152, and (iv) an electrical connector 154. Electrical connector 154 is utilized to enable electrical coupling of the pump 132 with the power supply 138. The main body portion 150 comprises (i) a housing 155 and (ii) the internal working parts of the pump 132. For example, in one exemplary embodiment, main body portion 150 comprises a pump stage portion 156 and a motor 158. At least a portion of the main body portion 150 is submersed in the liquid (e.g., water) contained in the receptacle 116, such that the pump 132 is effectively cooled. The motor 158 operates to engage the pump state portion 156. Engagement of the pump state portion 156 facilitates production of a pressure differential between the inlet 148 and outlet 152. By way of example, the pump state portion may include one or more turbines for pressurizing the liquid. Thus, in one example a pump main body portion comprises a housing and a motor coupled to a turbine, wherein the motor and turbine are housed within the housing.

As the motor 158 of the pump 132 operates to produce an increase in pressure, heat 160 is generated. In one embodiment, because the pump 132 is submersible, the fluid in the receptacle 116 acts to cool the pump 132 in at least two ways. For instance, the heat 160 is dissipated via conduction to the ambient fluids surrounding pump 132. Also, the heat 160 is dissipated by convection to the fluid as the fluid travels through pump stage portion 156 and motor 158, and eventually out through outlet 152. As the fluid, e.g., water, contacts the motor 158, the fluid cools the motor 158.

The fluid stored in receptacle 116 enters the pump 132 via the inlet 148. In one embodiment, inlet 148 has a filter (not shown) attached thereto to prevent potentially damaging particles from entering the pump 132. Once pressurized by the pump 132, the fluid exits the pump 132 via outlet 152. Supply hose 120 is coupled to outlet 152 to facilitate movement of the pressurized fluid from the pump 132 through the hose 120 and out the misting nozzles 122.

Figure 6:
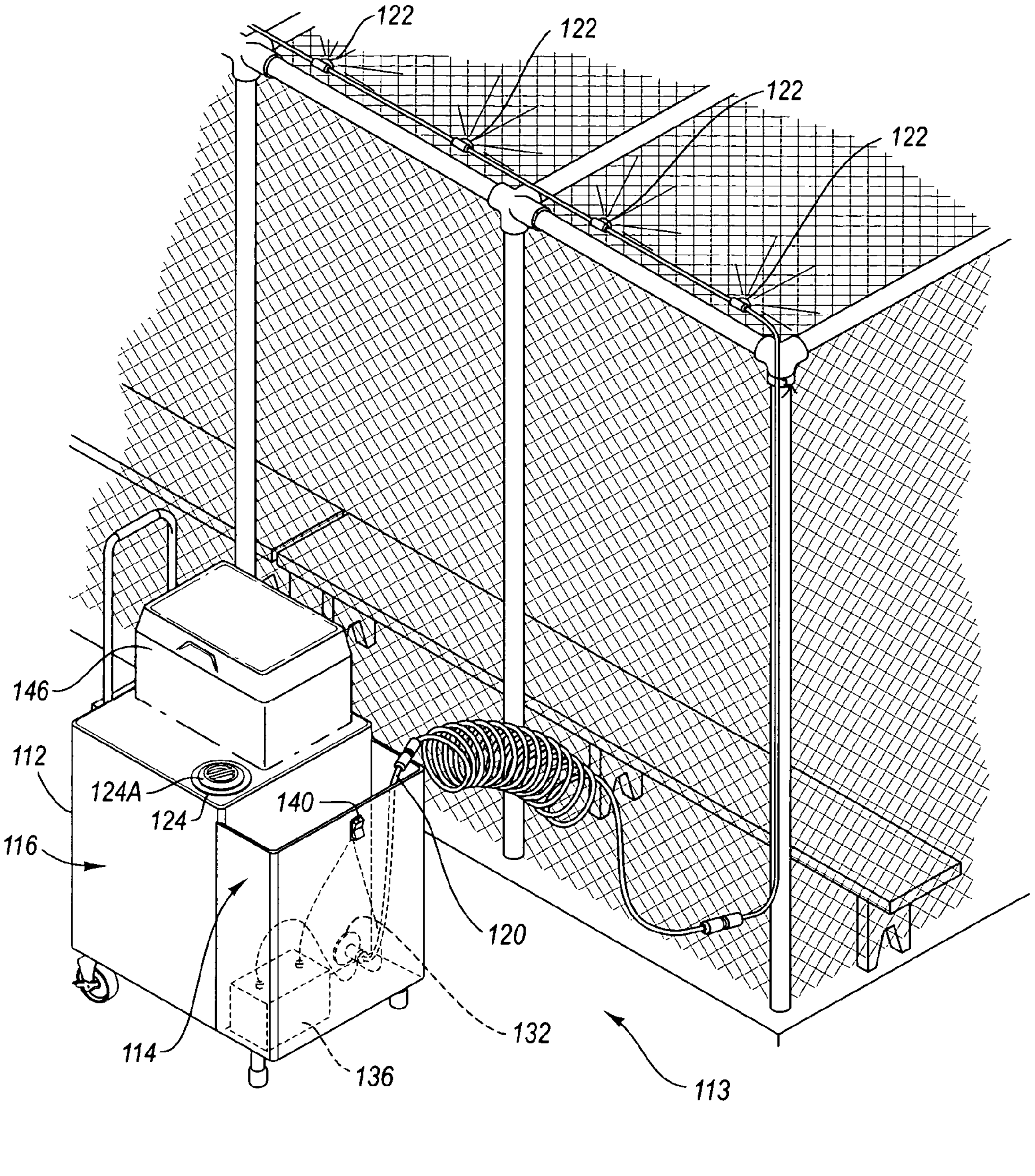
FIG. 6 shows an embodiment of a portable, self-contained misting system having a cooler attached thereto.

Shown in FIG. 6 is yet another embodiment of the present invention. In this embodiment, the misting system further includes a cooler 146 for storage of beverages, food, or other items a user may wish to keep cool. Cooler 146 is integrally coupled to the housing 112. In particular, the disclosed embodiment illustrates the cooler 146 being integrally coupled to the top of the receptacle 116. The cooler 146 being located on the top of the receptacle 116 enables user easy access to items stored in cooler 146. It is appreciated that cooler 146 location is not essential to the present invention and may be changed without departing from the scope and spirit of the invention.

In use, misting system 10, 110 is useful for a variety of different outdoor purposes, particularly when the weather becomes extremely hot. For example, misting system 10 can be used at picnics, athletic events, trade shows, and a variety of different games and activities in which it is desirable to cool ones body temperature.

For example, in one embodiment misting system 10, 110 is used in the dugout wherein the misting heads are placed on the fence or wall of the dugout in order to cool a baseball or softball team. Receptacle 16, 116 is filled with water and pump 32, 132 is turned on. Optionally, a lid is placed on inlet 24, 124. Pump 32, 132 creates water pressure in supply hose 20, 120 by pumping water from pump chamber 18, or alternatively, directly from receptacle 116.

In another embodiment, the plurality of misting nozzles 22, 122 are connected to an awning, a wall, or a fence, or other assembly enabling it to be used at a party or sales event, or family picnic.

We claim:

1. A portable self-contained misting system, the system comprising:

a housing having a receptacle configured to receive and store a liquid therein, and a pump chamber, wherein the pump chamber is in fluid communication with the receptacle;

a pump having a main body portion, the pump being in fluid communication with the pump chamber, wherein the main body portion is configured to be at least partially submersed in the liquid;

means for providing power to the pump; and at least one mister nozzle in fluid communication with the pump, wherein the receptacle and the pump chamber form an L-shape, the pump chamber forming the bottom leg of the L-shape.

2. The system of claim 1, wherein the fluid contained in the receptacle is water.

3. The system of claim 1, wherein the means for providing power is a battery.

4. A portable self-contained misting system as recited in claim 1, wherein a fluid supply hose couples the nozzle to the pump.

5. A misting system as recited in claim 4, wherein a dry compartment of the housing is configured to receive the supply hose therein.

6. A system as recited in claim 1, further comprising a switch for selectively activating the pump.

7. A portable self-contained misting system comprising:

a housing having an L-shaped dry compartment, a receptacle configured to receive liquid therein, and a pump chamber, the pump chamber being in fluid communication with the receptacle, wherein the receptacle has an opening configured to receive a liquid therethrough, the housing further having a lid configured to close the opening;

a pump in fluid communication with the pump chamber, wherein the pump has a main body portion that is configured to be at least partially submersed in the liquid;

a rechargeable power source disposed within the dry compartment, the rechargeable power source being electrically coupled to the pump, the power source being selectively activated such that the pump is selectively actuated; and a hose in fluid communication with the pump, the hose having at least one nozzle coupled thereto, the nozzle configured to provide a misting spray.

8. A system as recited in claim 7, wherein the L-shaped compartment is configured to receive the hose and the at least one nozzle therein.

9. A system as recited in claim 7, wherein a plurality of nozzles are in fluid communication with the hose.

10. A system as recited in claim 7, further comprising a telescoping handle coupled to the housing.

11. A system as recited in claim 7, further comprising an electrical cord that connects the rechargeable power source to the cigarette lighter of an automobile.

12. A portable misting system, the system comprising:

a fluid source having a fluid egress port;

a pump in fluid communication with the fluid source, wherein the pump has a main body portion that is configured to be at least partially submersed in the fluid and at least partially protruding through the fluid egress port;

means for providing power to the pump; and at least one mister nozzle in fluid communication with the pump.

13. The system of claim 12, wherein the fluid is water.

14. The system of claim 12, wherein the means for providing power is a battery.

15. The system of claim 14, further comprising an electrical cord that connects the battery to a cigarette lighter of an automobile.

16. The system of claim 12, wherein the means for providing power to the pump comprises an electrical cord, wherein the cord is electrically coupled to the pump and configured to be connected to an external power source.

17. The system of claim 12, wherein a fluid supply hose couples the nozzle to the pump.

18. The system of claim 12, further comprising a switch for selectively activating the pump.

19. A portable misting system, the system comprising:

a pump configured to be in fluid communication with a fluid source, wherein the pump has a main body portion, the main body portion being configured to be at least partially submersed in the fluid source and at least partially protruding through a fluid egress port in the fluid source;

means for providing power to the pump; and at least one mister nozzle in fluid communication with the pump.

20. The system of claim 19, wherein the means for providing power is a battery.

21. The system of claim 20, further comprising an electrical cord that connects the battery to a cigarette lighter of an automobile.

22. The system of claim 19, wherein the means for providing power to the pump includes a 110 volt plug, wherein the plug is electrically coupled to the pump and configured to be connected to an external power source such as a power outlet.

23. The system of claim 19, further comprising a receptacle configured to receive and store a liquid therein.

24. The system of claim 23, further comprising a dry compartment integrally coupled to the receptacle.

25. The system of claim 24, wherein a fluid supply hose couples the nozzle to the pump.

26. The system of claim 25, wherein the dry compartment of the housing is configured to receive the supply hose therein.

27. A system as recited in claim 19, further comprising a switch for selectively activating the pump.

28. A portable misting system, the system comprising:

a housing comprising:

a receptacle configured to receive and store a fluid; and a dry compartment coupled to the receptacle;

a pump coupled to the receptacle, wherein the pump is at least partially disposed within the receptacle, the pump having a main body portion, wherein the main body portion is configured to be at least partially submersed in the fluid;

a power supply for providing power to the pump;

at least one mister nozzle in fluid communication with the pump; and a supply hose coupling the nozzle to the pump, wherein the dry compartment is configured to receive and store the supply hose therein.

29. The system of claim 28, wherein the fluid is water.

30. The system of claim 28, wherein the power supply is a battery.

31. The system of claim 28, wherein the power supply includes a 110 volt plug that is electrically coupled to the pump and configured to be received into an external power outlet.

32. The system of claim 28, wherein the dry compartment is configured to store a battery therein, wherein the battery is the power supply.

33. A portable misting system, the system comprising:

a housing comprising:

a receptacle for storing water; and a dry compartment coupled to the receptacle;

a submersible pump protruding through a water egress port on a side of the receptacle, wherein the pump is configured to be in fluid communication with water stored in the receptacle;

a battery housed in the dry compartment, wherein the battery is electrically coupled to the pump;

at least one mister nozzle in fluid communication with the pump, wherein the at least one mister nozzle can be stored in the dry compartment when the misting system is not in use, wherein the water egress port is on a side of the receptacle that is substantially perpendicular to a top surface of the water in the receptacle when the portable misting system is in operation.

34. The system of claim 33, wherein the submersible pump comprises a motor and a pump stage portion.

35. The system of claim 34, wherein the motor and pump stage portion are configured to be wetted by the water when the submersible pump is at least partially submersed in the water.

36. The system of claim 34, wherein the motor is configured to be cooled by the water in the receptacle.

37. The system of claim 19, wherein the main body portion comprises a motor and a pump stage portion.

38. The system of claim 37, wherein the motor is configured to be cooled by the fluid source.

39. The system of claim 1, wherein the main body portion comprises a motor that is configured to be cooled by liquid in the receptacle.

40. The system of claim 12, wherein the main body portion comprises a motor that is configured to be cooled by fluid from the fluid source.

41. The system of claim 28, wherein the main body portion comprises a motor that is configured to be cooled by the fluid stored in the receptacle.

* * * * *

UNITED STATES PATENT AND TRADEMARK OFFICE

CERTIFICATE OF CORRECTION

PATENT NO. : 7,234,653 B2

APPLICATION NO. : 10/938477

DATED : June 26, 2007

INVENTOR(S) : Powell et al.

It is certified that error appears in the above-identified patent and that said Letters Patent is hereby corrected as shown below:

<u>Drawings</u>

Sheet 4, replace FIG. 3 with the figure depicted herein below wherein the battery has been labeled as --36-- and the wires as --38--

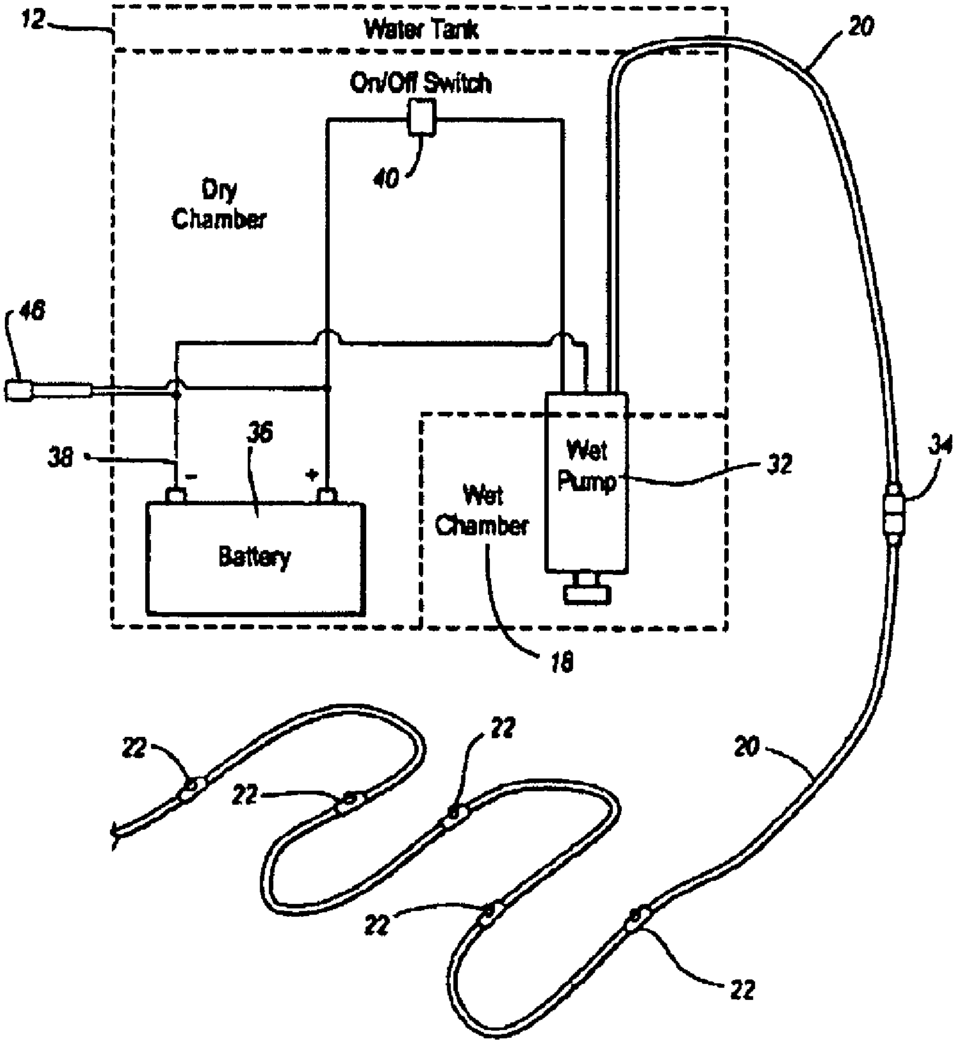

*Fig. 3*

UNITED STATES PATENT AND TRADEMARK OFFICE

CERTIFICATE OF CORRECTION

PATENT NO. : 7,234,653 B2
APPLICATION NO. : 10/938477
DATED : June 26, 2007
INVENTOR(S) : Powell et al.

It is certified that error appears in the above-identified patent and that said Letters Patent is hereby corrected as shown below:

Column 3
Line 44, after "system" change "12" to --10--

Column 4
Line 66, change "position" to --positioned--

Column 5
Line 11, change "26" to --28--
Line 32, change "receptacle 16, 116." to --receptacle 116.--

Column 6
Line 42, change "138" to --136--
Line 55, change "138" to --136--
Line 63, change "pump state" to --pump stage--
Line 66, change "pump state" to --pump stage--

Signed and Sealed this

Sixth Day of May, 2008

Jon W. Dudas

JON W. DUDAS
*Director of the United States Patent and Trademark Office*